(12) United States Patent
Tomko, Jr.

(10) Patent No.: US 10,913,789 B2
(45) Date of Patent: Feb. 9, 2021

(54) CHIMERIC PROTEINS AND THEIR USE IN IDENTIFYING ANTI-DEUBIQUITINASE COMPOUNDS

(71) Applicant: The Florida State University Research Foundation, Inc., Tallahassee, FL (US)

(72) Inventor: Robert J. Tomko, Jr., Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 16/861,932

(22) Filed: Apr. 29, 2020

(65) Prior Publication Data

US 2020/0331987 A1    Oct. 22, 2020

Related U.S. Application Data

(62) Division of application No. 16/152,881, filed on Oct. 5, 2018, now Pat. No. 10,676,519.

(60) Provisional application No. 62/569,211, filed on Oct. 6, 2017.

(51) Int. Cl.

| | |
|---|---|
| *C07K 14/81* | (2006.01) |
| *C12N 9/16* | (2006.01) |
| *C12N 15/62* | (2006.01) |
| *G01N 33/50* | (2006.01) |
| *A61K 38/48* | (2006.01) |

(52) U.S. Cl.
CPC .......... *C07K 14/8103* (2013.01); *A61K 38/48* (2013.01); *C12N 9/16* (2013.01); *C12N 15/62* (2013.01); *G01N 33/5008* (2013.01); *C07K 2319/03* (2013.01); *C07K 2319/50* (2013.01); *C07K 2319/74* (2013.01); *C07K 2319/95* (2013.01); *G01N 2500/02* (2013.01); *G01N 2500/10* (2013.01)

(58) Field of Classification Search
None
See application file for complete search history.

(56) References Cited

U.S. PATENT DOCUMENTS

2017/0050931 A1    2/2017    Deshaies et al.

OTHER PUBLICATIONS

Notice of Allowance issued for U.S. Appl. No. 16/152,881, dated Feb. 26, 2020.
Notice of Allowance issued for U.S. Appl. No. 16/152,881, dated Apr. 29, 2020.

*Primary Examiner* — Suzanne M Noakes
*Assistant Examiner* — Jae W Lee
(74) *Attorney, Agent, or Firm* — Meunier Carlin & Curfman LLC

(57) ABSTRACT

A chimeric protein having deubiquitinase activity, methods of identifying anti-deubiquitinase compounds using chimeric proteins, and kits comprising chimeric proteins are described herein. In one aspect, a chimeric protein comprises a mammalian deubiquitinase catalytic domain, a linker domain, and a non-human deubiquitinase proteasome binding domain. In another aspect, a method of identifying a compound having deubiquitinase inhibition activity comprises a) providing an assay for identifying a compound having deubiquitinase inhibition activity, wherein the assay comprises one or more biological cells comprising a chimeric protein comprising a mammalian deubiquitinase catalytic domain, a linker domain, and a non-human deubiquitinase proteasome binding domain; b) screening the assay with at least one compound; and c) identifying a compound having deubiquitinase inhibition activity based on survival of the biological cell. In another aspect, a kit comprises a biological cell comprising a herein disclosed chimeric protein.

9 Claims, 4 Drawing Sheets
Specification includes a Sequence Listing.

CHIMERIC PROTEINS AND THEIR USE IN IDENTIFYING ANTI-DEUBIQUITINASE COMPOUNDS

CROSS REFERENCE TO RELATED APPLICATIONS

This application claims the benefit of U.S. Provisional Patent Application Ser. No. 62/569,211, filed Oct. 6, 2017, the disclosure of which is expressly incorporated herein by reference in its entirety.

STATEMENT REGARDING FEDERALLY SPONSORED RESEARCH

This invention was made with government support under Grant No. 1R01GM118600 awarded by the National Institutes of Health (NIH). The Government has certain rights in the invention.

STATEMENT REGARDING ELECTRONIC FILING OF A SEQUENCE LISTING

A Sequence Listing in ASCII text format, submitted under 37 C.F.R. § 1.821, entitled 10850-004US1 2018 Oct. 4 Sequence listing.txt, 11,227 bytes in size, generated on Oct. 4, 2018 and filed via EFS-Web, is provided in lieu of a paper copy. The Sequence Listing is incorporated herein by reference into the specification for its disclosures.

FIELD

The disclosure herein relates to chimeric deubiquitinase proteins and methods for identifying anti-deubiquitinase compounds.

BACKGROUND

Ubiquitin is a small protein which functions at the level of protein regulation. Proteins are post-translationally modified by covalent conjugation with ubiquitin in a process referred to as ubiquitination. Among the regulatory functions of ubiquitin, polyubiquitination can mark a modified protein for proteasome-mediated degradation.

Deubiquitinase proteins play significant roles in cell-cycle regulation, signaling, DNA repair, chromatin remodeling, and other important biological functions. Deubiquitinase proteins serve to catalytically hydrolyze ubiquitin moieties from ubiquitinated proteins. In many cases, ubiquitination serves as a flag for delivery to the proteasome. Removal of ubiquitin moieties prior to interaction of the substrate with the proteasome can stave off degradation of that substrate. Notably, some deubiquitinases associate directly with the proteasome, and function to remove the polyubiquitin signal to permit completion of substrate degradation. In this way, deubiquitinases can either positively or negatively regulate degradation of proteasomal substrates.

Activity of the proteasome is deregulated in numerous human cancers. The human proteasomal Rpn11 deubiquitinase (also known as PSMD14, POH1. S13, Pad1, Mpr1) is a validated target for anticancer therapy. However, identification of potent, selective inhibitors has been thwarted by its poor in vitro activity and the lack of target-specific cell-based assays.

Cell-based assays which report directly on Rpn11 activity are currently unavailable. While biochemical screening methodologies have been previously employed, they require expensive reagents and do not address critical parameters necessary for further drug development. For instance, biochemical screens fail to address cell permeability, acute cellular toxicity, and other important factors required for identifying compounds useful for treating Rpn11-related diseases.

Thus, there is a need to address the aforementioned problems and other shortcomings associated with identification of anti-deubiquitinase compounds.

SUMMARY

Disclosed herein are chimeric proteins having deubiquitinase activity, and methods of identifying anti-deubiquitinase compounds using the chimeric proteins. The present disclosure addresses at least a portion of the problems described above by providing tools for cell-based assays to screen for anti-deubiquitinase compounds.

In one aspect, disclosed herein is a chimeric protein comprising a mammalian deubiquitinase catalytic domain, a linker domain, and a non-human deubiquitinase proteasome binding domain. In some embodiments, the deubiquitinase is Rpn11.

In another aspect, disclosed herein is a method of identifying a compound having deubiquitinase inhibition activity comprising: a) providing an assay for identifying a compound having deubiquitinase inhibition activity, wherein the assay comprises one or more biological cells comprising a chimeric protein comprising a mammalian deubiquitinase catalytic domain, a linker domain, and a non-human deubiquitinase proteasome binding domain; b) screening the assay with at least one compound; and c) identifying a compound having deubiquitinase inhibition activity based on survival of the biological cell. In some embodiments, the identified compound is an anticancer compound. In some embodiments, the assay comprises a first biological cell comprising humanized Rpn11 but lacking endogenous Rpn11 and Ubp6. In some embodiments, the assay comprises a second biological cell comprising humanized Rpn11 and endogenous Ubp6, but lacking endogenous Rpn11. In some embodiments, the assay comprises a third biological cell comprising genetically inactive humanized Rpn11 and endogenous Ubp6, but lacking endogenous Rpn11.

In another aspect, disclosed herein is a kit comprising a biological cell, wherein the biological cell comprises a chimeric protein comprising a mammalian deubiquitinase catalytic domain, a linker domain, and a non-human deubiquitinase proteasome binding domain.

The herein disclosed inventive chimeric proteins and methods allow for cell-based analysis of deubiquitinase (e.g., Rpn11) inhibition in screens, particularly high throughput screens, which has not thus far not been possible. The disclosed chimeric proteins and methods can be used for screens that are less effort-intense, more cost-effective, and less dependent on specialized equipment than current biochemical screens. The short doubling time and low cost of yeast culture facilitates screening of large chemical libraries at a fraction of the cost compared to current biochemical screens. Further, disclosed methods comprising a cell-based assay de novo selects for cell membrane-permeable compounds, which is required for deubiquitinase inhibitor development.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE FIGURES

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

DETAILED DESCRIPTION

Figure 1:
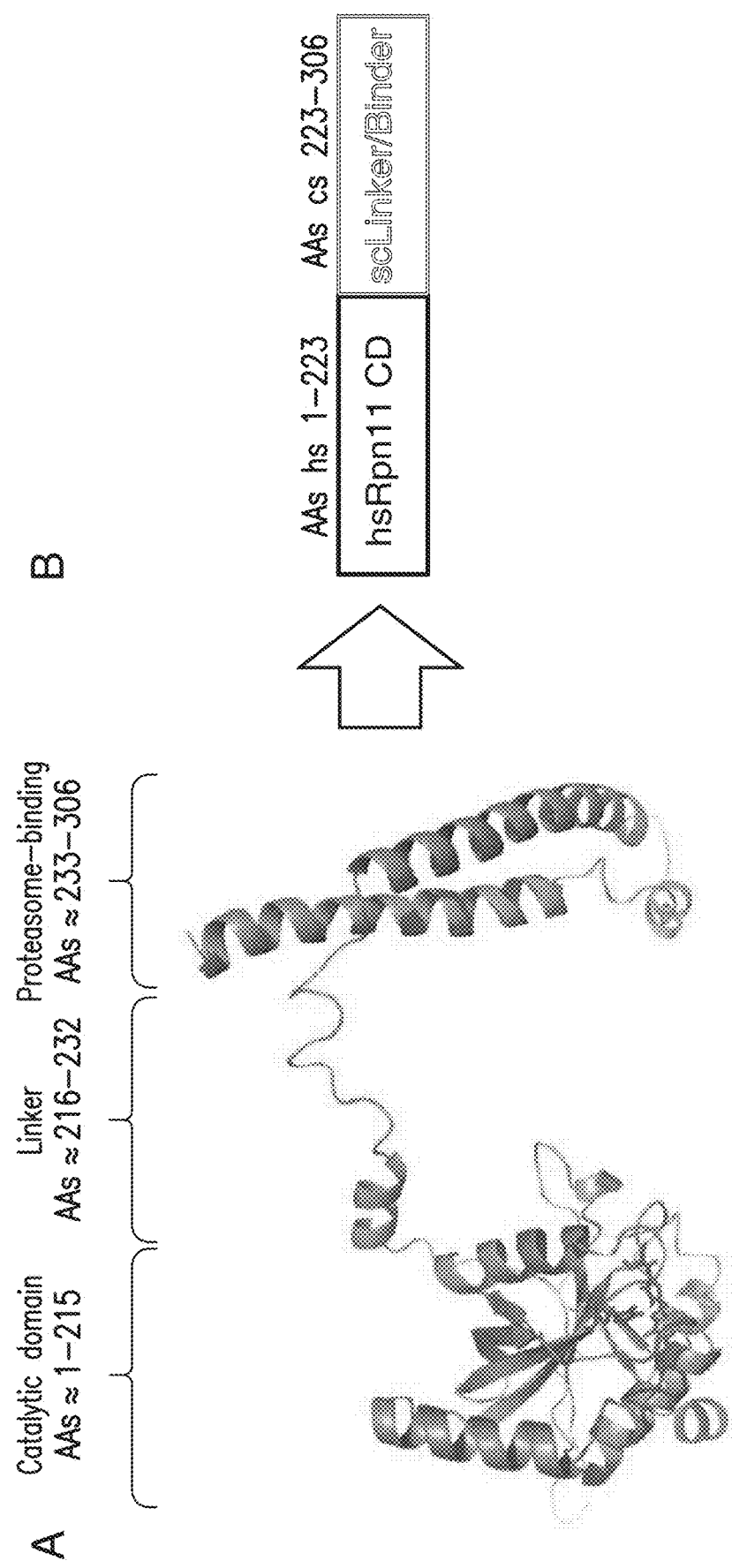
FIG. 1 is a schematic showing the design of a chimeric humanized Rpn11 ("hRpn11") for expression in yeast.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Definitions

Unless defined otherwise, all technical and scientific terms used herein have the same meaning as commonly understood to one of ordinary skill in the art to which this invention belongs. The following definitions are provided for the full understanding of terms used in this specification.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polypeptide is disclosed and discussed and a number of modifications that can be made to the polypeptide are discussed, specifically contemplated is each and every combination and permutation of the polypeptide and the modifications that are possible unless specifically indicated to the contrary. Thus, if a class of polypeptides A, B, and C are disclosed as well as a class of polypeptides D, E, and F and an example of a combination polypeptide, or, for example, a combination polypeptide comprising A-D is disclosed, then even if each is not individually recited, each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment, the terms are defined to be within 10% of the associated value provided. In another non-limiting embodiment, the terms are defined to be within 5%. In still another non-limiting embodiment, the terms are defined to be within 1%.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

"Peptide," "protein," and "polypeptide" are used interchangeably to refer to a natural or synthetic molecule comprising two or more amino acids linked by the carboxyl group of one amino acid to the alpha amino group of another. The amino acids may be natural or synthetic, and can contain chemical modifications such as disulfide bridges, substitution of radioisotopes, phosphorylation, substrate chelation (e.g., chelation of iron or copper atoms), glycosylation, acetylation, formylation, amidation, biotinylation, and a wide range of other modifications. A polypeptide may be attached to other molecules, for instance molecules required for function. Examples of molecules which may be attached to a polypeptide include, without limitation, cofactors, polynucleotides, lipids, metal ions, phosphate, etc. Non-limiting examples of polypeptides include peptide fragments, denatured/unstructured polypeptides, polypeptides having quaternary or aggregated structures, etc. There is expressly no requirement that a polypeptide must contain an intended function; a polypeptide can be functional, non-functional, function for unexpected/unintended purposes, or have unknown function. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). The terms "polypeptide sequence" or "amino acid sequence" are an alphabetical representation of a polypeptide molecule.

"Polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide limy be further modified after polymerization, such as by conjugation with a labeling component. A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule.

"Subject" includes animals such as mammals, including, but not limited to, primates (e.g., humans), cows, sheep, goats, horses, dogs, cats, rabbits, rats, mice and the like. In some embodiments, the subject is a human.

"Transformation" of a cellular organism with DNA means introducing DNA into an organism so that at least a portion of the DNA is replicable, either as an extrachromosomal element or by chromosomal integration. "Transfection" of a cellular organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of E. coli. Typical eukaryotic host cells are mammalian, such as Chinese hamster ovary or cells of human origin. In some embodiments, the eukaryotic host cell is a yeast cell. The introduced DNA sequence may be from the same species as the host cell of a different species from the host cell, or it may be a hybrid DNA sequence, containing some foreign and some homologous DNA.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an ailment.

Chimeric Proteins

In one aspect, disclosed herein is a chimeric protein. The chimeric protein contains a mammalian deubiquitinase catalytic domain. Further, the chimeric protein contains a linker domain and a non-human deubiquitinase proteasome binding domain.

Deubiquitinases are a large family of proteins prevalent in eukaryotic cells. The deubiquitinase can be any deubiquitinase protein, or any human deubiquitinase protein. There are approximately 79 functional deubiquitinase proteins in humans. Examples of human deubiquitinases include USP1, USP2, USP3, USP4, USP5, USP6, USP7, USP8, USP9X, USP9Y, USP10, USP11, USP12, USP13, USP14, USP15, USP16, USP17, USP17L2, USP17L3, USP17L4, USP17L5, USP17L7, USP17L8, USP18, USP19, USP20, USP21, USP22, USP23, USP24, USP25, USP26, USP27X, USP28, USP29, USP30, USP31, USP32, USP33, USP34, USP35, USP36, USP37, USP38, USP39, USP40, USP41, USP42, USP43, USP44, USP45, USP46, OTUB1, OTUB2, ATXN3, ATXN3L, BAP1, UCHL1, UCHL3, UCHL5, and Rpn11. In some embodiments, the deubiquitinase is Rpn11.

Mammalian (e.g., human) Rpn11 contains at least three domains: a catalytic domain, a linker domain, and a proteasome binding domain. Compounds having anti-deubiquitinase activity can target any one or more portions of Rpn11. However, the catalytic domain may be a promising target of Rpn11 for disruption of deubiquitinase activity.

The herein disclosed chimeric protein comprises a mammalian deubiquitinase catalytic domain. In some embodiments, the mammalian deubiquitinase catalytic domain is a human deubiquitinase catalytic domain. In some embodiments, the catalytic domain of human Rpn11 is used.

It has been observed that expression in host cells for cloning (e.g., *E. coli*) of the human gene encoding Rpn11 can be toxic. In some instances, a "humanized" polynucleotide encoding the mammalian deubiquitinase catalytic domain can be used to address these and other issues. The term "humanized" as used herein refers to a polynucleotide sequence which is not identical to a human polynucleotide sequence, but codes for a polypeptide having an amino acid sequence which is identical to a human amino acid sequence. The term "humanized" may also refer to the amino acid sequence or polypeptide encoded by a humanized polynucleotide. Thus, in some embodiments, the mammalian deubiquitinase catalytic domain can be a polypeptide encoded by a humanized polynucleotide synthetically created or derived from a non-human organism. Any non-human organism having a polynucleotide encoding the deubiquitinase catalytic domain of Rpn11 which can be humanized to encode human deubiquitinase catalytic domain of Rpn11 can be used. For example and without limitation, an amphibian (e.g., *Xenopus laevis*) gene encoding Rpn11 can be modified to express a polypeptide having an identical amino acid sequence as that of the human Rpn11 catalytic domain. In such an embodiment, the amphibian-based polynucleotide may have lower toxicity in host cells compared to a human-based polynucleotide, even though the polypeptides (e.g., human Rpn11 catalytic domain) encoded by the two polynucleotides have identical amino acid sequences. Polymerase chain reaction (PCR)-based methods to modify polynucleotide sequences to alter polypeptide amino acid sequences are well known in the art.

Mammalian (e.g., human) Rpn11 contains a linker domain. The linker domain of the chimeric protein is not particularly limited, and needs only to link a polypeptide comprising a deubiquitinase catalytic domain and a polypeptide comprising a non-human deubiquitinase proteasome binding domain. As such, any linker domain suitable for this purpose can be used. In some embodiments, the linker domain comprises a non-human deubiquitinase linker domain. In some embodiments, the linker domain comprises a non-human Rpn11 linker domain. In some embodiments, the linker domain comprises a yeast Rpn11 linker domain. In embodiments in which the chimeric protein is to be expressed in yeast cells (e.g., *Saccharomyces cerevisiae*), a linker domain comprising a *Saccharomyces cerevisiae* Rpn11 linker domain can be a particularly suitable linker domain.

Mammalian (e.g., human) Rpn11 contains a proteasome binding domain which mediates docking of Rpn11 onto the proteasome. The chimeric protein can contain any deubiquitinase proteasome binding domain suitable for constructing a chimeric protein having deubiquitinase activity in a biological host cell. In some embodiments, the deubiquitinase proteasome binding domain is a non-human deubiquitinase proteasome binding domain. In some embodiments, the deubiquitinase proteasome binding domain is a non-human Rpn11 proteasome binding domain. A particularly useful embodiment comprises a deubiquitinase proteasome binding domain which is identical to the Rpn11 proteasome binding domain of the biological host cell in which the chimeric protein is to be expressed. For instance, in embodiments in which the chimeric protein is to be expressed in yeast cells (e.g., *Saccharomyces cerevisiae*), a non-human deubiquitinase proteasome binding domain comprising a *Saccharomyces cerevisiae* Rpn11 proteasome binding domain can be a particularly suitable iron-human deubiquitinase proteasome binding domain.

Without limitation, a particularly useful chimeric protein according to the present disclosure is exemplified by the amino acid sequence of SEQ ID NO: 1. The polypeptide described by SEQ ID NO: 1 contains the major domains of mammalian Rpn11. An N-terminal catalytic domain (comprising amino acids 1-215) is fused to a linker domain (comprising amino acids 216-232), while the linker domain is in turn fused to a C-terminal proteasome binding domain (comprising amino acids 233-306) (FIG. 1). More specifically, the polypeptide of SEQ ID NO: 1 contains an N-terminal human Rpn11 catalytic domain fused to a *S. cerevisiae* Rpn11 linker domain, wherein the linker domain is in turn fused to a C-terminal *S. cerevisiae* Rpn11 proteasome binding domain.

Due to redundancy in the genetic code, the amino acid sequence described by SEQ ID NO: 1 can be encoded by a wide array of polynucleotides. Without limitation, a particularly useful polynucleotide encoding the herein disclosed chimeric protein (e.g., the chimeric protein described by SEQ ID NO: 1) is exemplified by the polynucleotide sequence of SEQ ID NO: 2.

In some embodiments, the chimeric protein comprises an amino acid sequence comprising at least 80 percent, 85 percent, 90 percent, 95 percent, 98 percent, or at least 99 percent identity to SEQ ID NO: 1. In some embodiments, the chimeric protein comprises an amino acid sequence having 100 percent identity to SEQ ID NO: 1.

In some embodiments, the chimeric protein is encoded by a polynucleotide comprising at least 80 percent, 85 percent, 90 percent, 95 percent, 98 percent, or at least 99 percent identity to SEQ ID NO: 2. In some embodiments, the chimeric protein is encoded by a polynucleotide having 100 percent sequence identity to SEQ ID NO: 2.

The chimeric protein can be expressed in a biological cell. As an example and without limitation, a polynucleotide of SEQ ID NO: 2 can be transformed into a biological cell, and the protein transcription and translation machinery of the biological cell can express a polypeptide of SEQ ID NO: 2 therefrom. In some embodiments, the biological host cell is a non-human eukaryotic cell, or more specifically, a yeast cell, or more specifically, a Saccharomyces cerevisiae cell.

It can be advantageous to reduce interference from endogenous deubiquitinases in a screen for deubiquitinase inhibitors in a biological cell comprising the chimeric protein disclosed herein. For example, in an embodiment in which a Saccharomyces cerevisiae cell contains a polynucleotide of SEQ ID NO: 1, which expresses a polypeptide of SEQ ID NO: 2, it can be advantageous to reduce or eliminate expression of endogenous S. cerevisiae Rpn11, by, for example, genetic modification. Thus, in some embodiments, a biological cell (e.g., a S. cerevisiae cell) can be genetically modified to replace endogenous Rpn11 (e.g., by genetic knock-out strategies) with a herein disclosed chimeric protein. In some such embodiments, the chimeric protein comprises a humanized Rpn11 catalytic domain, the chimeric protein occasionally referred to herein as "hRpn11." In some embodiments, the biological cell may be further genetically modified to reduce or eliminate expression of a second endogenous deubiquitinase, for example, Ubp6 (homologous to USP14 in humans). One advantage of such a biological cell is its use in a chemical-genetic cell-based screen to identify selective inhibitors of human Rpn11 and deubiquitinating activity.

It is understood that the chimeric protein of the present disclosure can be used in combination with the various compositions, methods, products, and applications disclosed herein.

Methods

In another aspect, disclosed herein is a method of identifying a compound having deubiquitinase inhibition activity comprising: a) providing an assay for identifying a compound having deubiquitinase inhibition activity, wherein the assay comprises one or more biological cells comprising a chimeric protein comprising a mammalian deubiquitinase catalytic domain, a linker domain, and a non-human deubiquitinase proteasome binding domain; b) screening the assay with at least one compound; and c) identifying a compound having deubiquitinase inhibition activity based on survival of the biological cell.

As discussed, deubiquitinases have been linked to cancer. As such, deubiquitinase inhibition activity of a compound identified in the methods can also be anticancer activity. Typically, the deubiquitinase inhibition activity of a compound identified in the methods is due to inhibition of the chimeric protein present in the biological cell.

The chimeric protein can be any herein disclosed chimeric protein.

The biological cell is typically a host cell for the expression of the chimeric protein. The biological cell is preferably one in which a screen of compounds (e.g., high throughput screen) can easily be performed. In some embodiments, the biological cell is a non-human eukaryotic cell, or more specifically, a yeast cell, or more specifically, a Saccharomyces cerevisiae cell.

In some embodiments, the biological cell (e.g., a S. cerevisiae cell) can be genetically modified to replace endogenous Rpn11 (e.g., by genetic knock-out strategies) with a herein disclosed chimeric protein. In some such embodiments, the chimeric protein comprises a humanized Rpn11 catalytic domain ("hRpn11"). In some embodiments, the biological cell may be further genetically modified to reduce or eliminate expression of a second endogenous deubiquitinase, for example, Ubp6 (homologous to USP14 in humans).

Thus, in some embodiments, the biological cell lacks a first endogenous polynucleotide encoding a first functional deubiquitinase, and a second endogenous polynucleotide encoding a second functional deubiquitinase. In some embodiments, the biological cell lacks the first functional deubiquitinase Rpn11. In some embodiments, the biological cell lacks the second functional deubiquitinase Ubp6.

Figure 2:
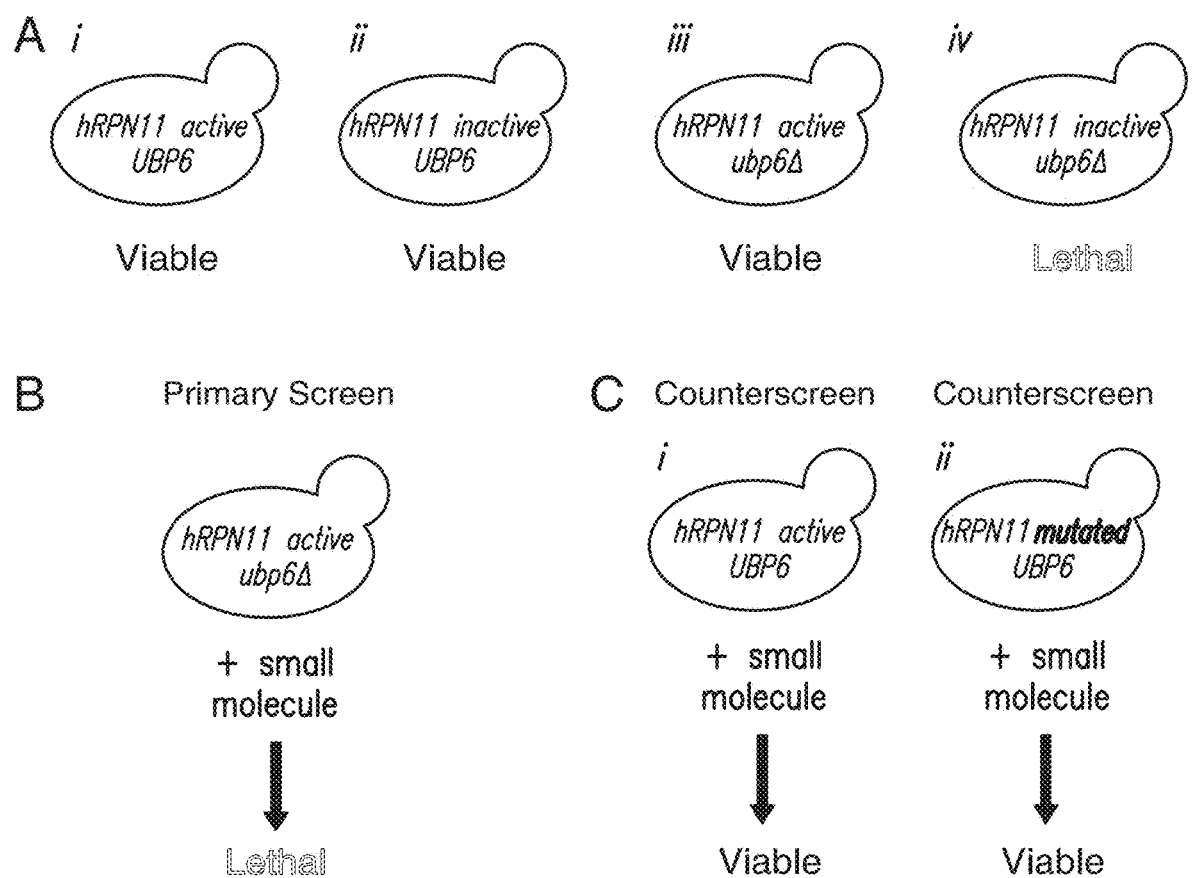
FIG. 2 is a schematic showing the rationale for and design of a chemical-genetic screen for human Rpn11 inhibitors.
Figure 3:
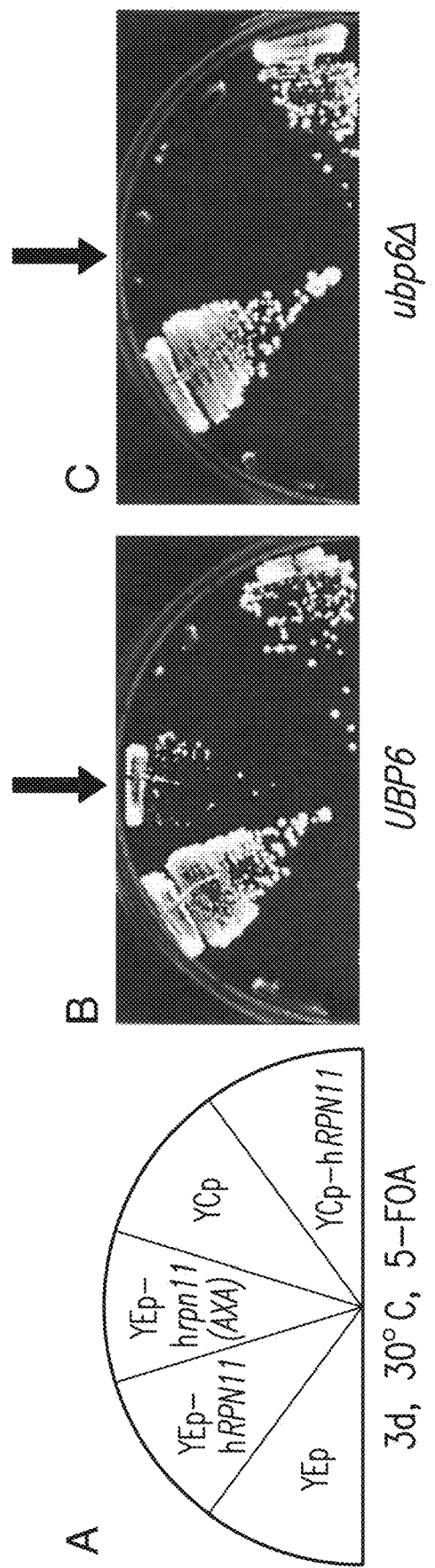
FIG. 3 shows validation of the technology and proof-of-principle for the proposed chemical-genetic approach.

In baker's yeast (S. cerevisiae), deletion of the endogenous yeast Rpn11 gene is lethal, but inhibition of Rpn11 deubiquitinating activity is not. Inhibition of Rpn11 activity is lethal only when a second deubiquitinase, UBP6, is deleted (FIG. 2A). Importantly, this synthetic lethal relationship is maintained in yeast harboring hRpn11 (FIG. 3). Thus, a selective inhibitor of human Rpn11 would be lethal in the hRpn11 strain lacking UBP6 (primary screen strain), but nontoxic in a strain containing UBP6 and harboring inactivating point mutations in hRpn11 (counterscreening strain) (FIG. 2B). By measuring cell growth in the presence of potential inhibitors using any commercially available plate reader, a high throughput cell-based screen for compounds selectively inhibiting hRpn11 can be enacted.

In the above described cell-based screen (e.g., a high throughput screen), the identifying step can be performed based on simple cell survival. Thus, optionally, the identifying step c) comprises selecting the compound having deubiquitinase inhibition activity based on death of the biological cell when cultured in the presence of the compound. Survival of a primary screen biological cell when exposed to a compound indicates the compound does not have sufficient deubiquitinase inhibition activity (or other factors, such as insufficient membrane permeability).

The methods can benefit from inclusion of more than one biological cell. In some embodiments, the methods include a first biological cell and a second biological cell. In sonic embodiments, the methods include a first biological cell, a second biological cell, and a third biological cell.

Optionally, the first biological cell contains a herein described chimeric protein but lacks a first endogenous polynucleotide encoding a first functional deubiquitinase (e.g., Rpn11), and a second endogenous polynucleotide encoding a second functional deubiquitinase (e.g., Ubp6). The first biological cell is particularly useful as a primary screen strain. At least because the first biological cell having hRpn11 contains a protein having functional Rpn11 deubiquitinase activity, the first biological cell is viable (FIG. 2Aiii). If a compound screened in the method inhibits hRpn11, the first biological cell will not survive (FIG. 2B).

Optionally, the second biological cell contains a herein described chimeric protein, lacks the first endogenous polynucleotide encoding the first functional deubiquitinase (e.g., Rpn11), but contains the second endogenous polynucleotide encoding the second functional deubiquitinase (e.g., Ubp6). The second biological cell is particularly useful as a counterscreen strain. At least because the second biological cell contains both hRpn11 and Ubp6, a compound which specifically inhibits Rpn11 activity will not result in death of the second biological cell (FIG. 2Ci). However, a compound which is lethal to the first biological cell and the second biological cell is a compound which does not specifically inhibit Rpn11 activity. Thus, the identifying step c) can optionally include selecting a compound having deubiquitinase inhibition activity based on death of the first biological cell and survival of the second biological cell when the first and second biological cells are cultured in the presence of the compound.

Optionally, the third biological cell contains a herein described chimeric protein, lacks the first endogenous polynucleotide encoding the first functional deubiquitinase (e.g., Rpn11), contains the second endogenous polynucleotide encoding the second functional deubiquitinase (e.g., Ubp6), but differs from the second biological cell in that the chimeric protein is genetically inactivated, resulting in a chimeric protein lacking deubiquitinase activity (also referred to as "catalytically inactive"). The third biological cell is particularly useful as a counterscreen strain. At least because the third biological cell contains Ubp6, a compound which specifically inhibits Rpn11 activity will not result in death of the third biological cell (FIG. 2Cii). However, a compound which is lethal to the first biological cell and the third biological cell is a compound which does not specifically inhibit Rpn11 activity. Thus, the identifying step c) can optionally include selecting the compound having anticancer activity based on death of the first biological cell and survival of the third biological cell (or second and third biological cells) when the first and third biological cells (or first, second, and third biological cells) are cultured in the presence of the compound.

Catalytically inactive hRpn11 can be obtained by introducing mutations in the hRpn11 polynucleotide coding sequence. Numerous inactivating point mutations, or combinations of inactivating point mutations, can be made in hRpn11 which result in catalytically inactive hRpn11 protein. For example, mutation of codons encoding histidine 113 and histidine 115 in SEQ ID NO: 4 to alanine residues shown in SEQ ID NO: 5 results in catalytically inactive hRpn11 (occasionally referred to herein as hRpn11 (AXA)).

In some or further embodiments, any biologic cell described herein can have mutations in genes encoding for proteins which efflux molecules from the biological cell. For example, the yeast S. cerevisiae genome encodes at least 15 full-size ABC family transporter proteins (AUS1, BAT1, BTP1, NFT1, PDR5, PDR10, PDR11, PDR12, PDR15, PDR18, SNQ2, STE6, VMR1, YCF1, YOL075C, and YOR1). ABC family transport proteins export various chemicals and biomacromolecules from the yeast cytosol into the extracellular environment. Several of these transporters, including but not limited to PDR5, SNQ2, and YOR1, promote resistance to the pharmacological or toxic effects of drug-like small molecules. Resistance likely occurs via the ABC transport activity of these proteins.

In some instances, it can be advantageous to assay small molecules for a pharmacological activity in a biological cell genetically inactivated (e.g., gene deletion) for one or more ABC transporters because their genetic inactivation can enhance the accumulation of compounds (e.g., drug-like small molecules) in the biological cell. This in turn increases the likelihood that a compound with a desired pharmacological activity(ies) would be discovered in that assay at least in part because the intracellular concentration of the compound remains elevated.

In some or further embodiments, the biological cell contains a genetically inactivated ABC transporter. In some or further embodiments, the first biological cell, the second biological cell, or the third biological cell contains a genetically inactivated ABC transporter. In some or further embodiments, any two or more of the first biological cell, the second biological cell, and the third biological cell contain a genetically inactivated ABC transporter. In some or further embodiments, each of the first biological cell, the second biological cell, and the third biological cell contain a genetically inactivated ABC transporter. In some or further embodiments, the biological cell contains two or more genetically inactivated ABC transporters. In some or further embodiments, the biological cell contains three or more genetically inactivated ABC transporters.

The ABC transporter can be, but is not limited to, AUS1, BAT1, BTP1, NFT1, PDR5, PDR10, PDR11, PDR12, PDR15, PDR18, SNQ2, STE6, VMR1, YCF1, YOL075C, YOR1, and any hereinafter identified ABC transporter in the S. cerevisiae genome. In some embodiments, the ABC transporter is PDR5, SNQ2, or YOR1.

In some or further embodiments, results of a method performed using any biological cell containing a first genetically inactivated ABC transporter can be compared to results of a method performed using any biological cell containing a second genetically inactivated ABC transporter. In some or further embodiments, results of a method performed using any biological cell containing a first genetically inactivated ABC transporter can be compared to results of a method performed using any biological cell containing a first and a second genetically inactivated ABC transporter.

Many high throughput screens include a library of chemical compounds having different solubility in different solvents. A common solvent used to solve this issue is dimethyl sulfoxide ("DMSO"). However, DMSO can be toxic to biological cells. Thus, it is advantageous if the biological cell is resistant to levels of DMSO which are used to dissolve compounds in a library. Optionally, the biological cell has a similar growth rate in media comprising up to one percent dimethyl sulfoxide compared to media comprising zero percent dimethyl sulfoxide.

Also disclosed herein is a method of treating a subject. In some embodiments, the subject has a disease. Optionally, the disease can be treated by inhibiting a deubiquitinase. Optionally, the disease is cancer. In some embodiments, the subject is in need of deubiquitinase inhibition activity for the treatment of a disease. In some embodiments, the method comprising administering to the subject a compound identified by the herein disclosed methods to identify a compound having deubiquitinase inhibition activity.

Kits

Also disclosed herein is a kit comprising a biological cell, wherein the biological cell comprises a chimeric protein comprising a mammalian deubiquitinase catalytic domain, a linker domain, and a non-human deubiquitinase proteasome binding domain.

The chimeric protein can be any herein disclosed chimeric protein.

Optionally, the biological cell is a yeast cell, particularly S. cerevisiae. Optionally, the biological cell includes a first biological cell and a second biological cell. Optionally, the biological cell includes a first biological cell, a second biological cell, and a third biological cell. Optionally, the first biological cell contains a herein described chimeric protein but lacks a first endogenous polynucleotide encoding a first functional deubiquitinase (e.g., Rpn11), and a second endogenous polynucleotide encoding a second functional deubiquitinase (e.g., Ubp6). Optionally, the second biological cell contains a herein described chimeric protein, lacks the first endogenous polynucleotide encoding the first functional deubiquitinase (e.g., Rpn11), but contains the second endogenous polynucleotide encoding the second functional deubiquitinase (e.g., Ubp6). Optionally, the third biological cell contains a herein described chimeric protein, lacks the first endogenous polynucleotide encoding the first functional deubiquitinase (e.g., Rpn11), contains the second endogenous polynucleotide encoding the second functional deubiquitinase (e.g., Ubp6), but differs from the second biological cell in that the chimeric protein is genetically inactivated, resulting in a chimeric protein lacking deubiquitinase activity.

The kit, in some embodiments, further comprises a library of compounds. Optionally, the library of compounds may be screened by the herein disclosed methods.

Elements and components of the kit may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more reaction or storage buffers, or media for cell growth. Reagents may be provided in a form that is usable in a particular assay, or in a form that requires addition of one or more other components before use (e.g. in concentrate or lyophilized form).

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Efforts have been made to ensure accuracy with respect to numbers (e.g., amounts, temperatures, etc.); however, some errors and deviations should be accounted for. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

In a first example, a chimeric humanized Rpn11 (hRpn11) polypeptide was constructed. The hRpn11 was optimized for expression of human Rpn11 catalytic domain in yeast cells. The pseudoatomic structure of human Rpn11 is shown in FIG. 1A (PDB=5L4K). Key catalytic residues are shown as stick side-chains. The globular catalytic domain consists of amino acids approx. 1 to 215. This globular catalytic domain is connected via a poorly structured linker (amino acids 216-232) to a helical proteasome-binding domain (amino acids 233-306) that mediates docking of Rpn11 into the proteasome. A chimeric human-yeast Rpn11 ("hRpn11") was created by fusing the linker and proteasome-binding sequence from yeast Rpn11 in frame with the globular catalytic domain of human Rpn11. Amino acids 1-223 of the human Rpn11 sequence were fused with amino acids 223-306 of the S. cerevisiae Rpn11 sequence.

Example 2

In a second example, a chemical-genetic screen for human Rpn11 inhibitors was constructed. The screen is based on synthetic-lethal relationships between hRpn11 and UBP6 (FIG. 2A). When hRpn11 is active and UBP6 is intact (FIG. 2Ai), cells are viable. If hRpn11 is inactive (FIG. 2Aii) or if UBP6 is deleted (ubp6L1; FIG. 2Aiii), cells remain viable. When hRpn11 is inactive and UBP6 is deleted, synthetic lethality occurs (FIG. 2Aiv). The chemical-genetic screening strategy to identifies human Rpn11 inhibitors by addition of candidate small molecules from a library to a primary screen yeast strain and at least one counterscreen yeast strain. A chemical inhibitor of hRpn11 activity is lethal when UBP6 is deleted (FIG. 29), but is not lethal if UBP6 is intact (FIG. 2Ci and ii). This holds true even when hRpn11 is genetically inactivated (FIG. 2Cii). Small molecules demonstrating nonselective toxicity will impair health in both the primary screen and at least one counterscreen, whereas inactive molecules will have no effect in the primary screen.

Example 3

In a third example, yeast strains were plated for evaluated for growth to demonstrate the synthetic-lethal relationships between hRpn11 and UBP6 discussed in Example 2. Genetic inactivation of hRpn11 is lethal only when UBP6 is deleted. FIG. 3A shows the plating arrangement of yeast strains in FIGS. 3B and C. Yeast provided with active hRpn11 at high (YEp-hRPN11) or low (Ycp-hRPN11) expression levels as the only copy were viable, whereas yeast provided with an empty vector (YEp or YCp) were not viable. Provision of genetically inactivated hRPN11 (YEp-hrpn11(AXA)) were viable when UBP6 was intact (FIG. 3B; arrow), but not when it was deleted (FIG. 3C; arrow).

Example 4

Figure 4:
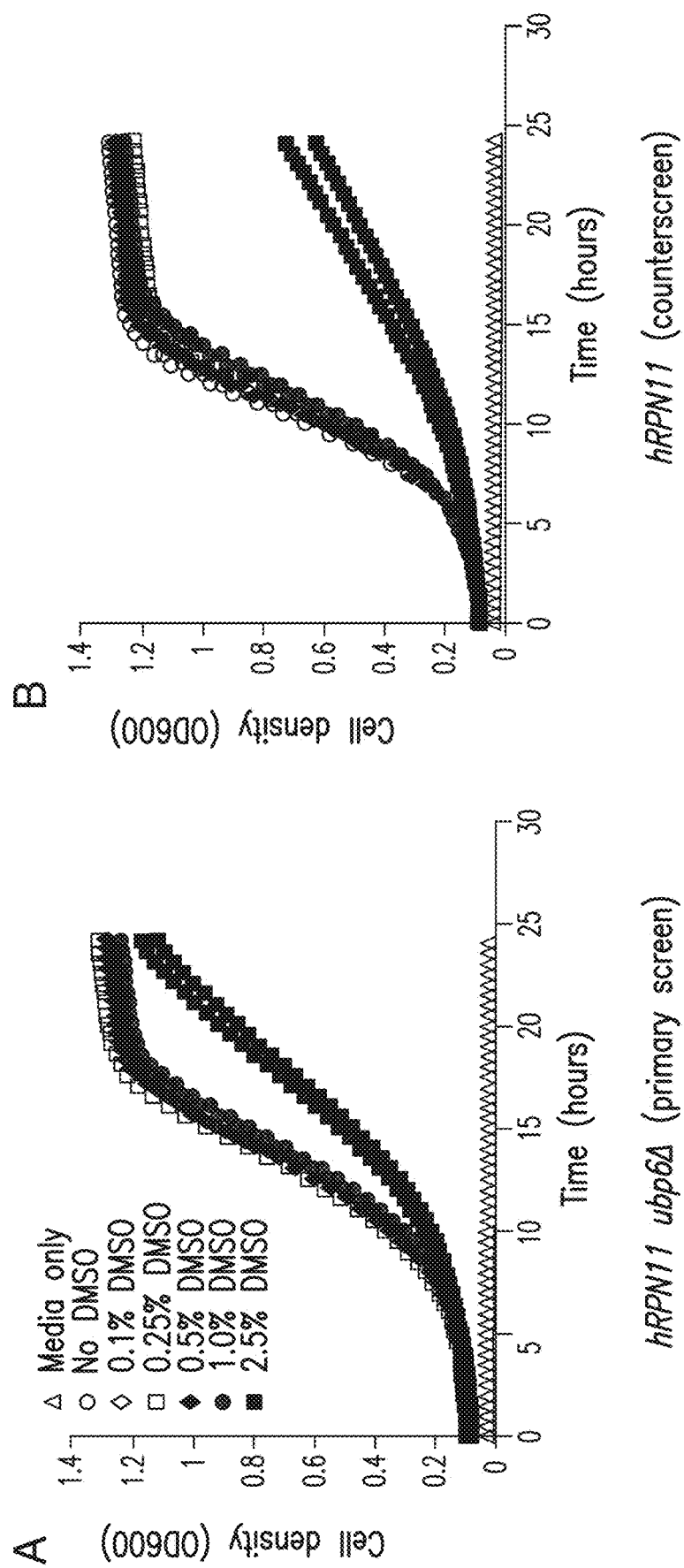
FIG. 4 is a set of graphs showing miniaturization and DMSO tolerance of the screening strains.

In a fourth example, yeast strains were evaluated for tolerance of a commonly used solvent in high throughput screens. The primary screen (FIG. 4A) and counterscreen (FIG. 4B) strains were grown in sextuplicate in microtiter plates in the presence of the indicated concentrations of the organic solvent dimethylsulfoxide (DMSO). Cell density was monitored over 24 hours as an indicator of cell growth. No statistical differences in growth rate, time to saturation, or saturation cell density were observed for concentrations of DMSO up to 1%.

Publications cited herein are hereby specifically incorporated by reference in their entireties and at least for the material for which they are cited.

Lastly, it should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

SEQUENCES
hRpn11 amino acid sequence
SEQ ID NO: 1
MDRLLRLGGGMPGLGQGPPTDAPAVDTAEQVYISSLALLKMLKHGRAGVP

MEVMGLMLGEFVDDYTVRVIDVFAMPQSGTGVSVEAVDPVFQAKMLDMLK

QTGRPEMVVGWYHSHPGFGCWLSGVDINTQQSFEALSERAVAVVVDPIQS

VKGKVVIDAFRLINANMMVLGHEPRQTTSNLGHLNKPSIQALIHGLNRHY

YSITINYRKNELEQKMLLNLHKK<u>SGLKMYDYEEKEESNLAATKSMVKIAE

QYSKRIEEEKELTEEELKTRYVGRQDPKKHLSETADETLENNIVSVLTAG

VNSVAIK</u>
Non-underlined sequences are identical to a portion
of the human Rpn11 amino acid sequence. Underlined
sequences are identical to a portion of the yeast
(*Saccharomyces cerevisiae*) Rpn11 amino acid
sequence.

cDNA encoding hRpn11
SEQ ID NO: 2
ATGGACCGACTTTTAAGGCTTGGAGGAGGGATGCCTGGACTTGGCCAGGG

CCCTCCCACTGATGCTCCTGCAGTGGATACTGCCGAACAGGTTTATATCT

CCTCCCTGGCTTTGCTCAAGATGCTAAAACACGGACGAGCTGGTGTCCCA

ATGGAAGTCATGGGACTGATGCTGGGAGAGTTTGTGGATGATTACACAGT

CAGGGTCATTGATGTTTTTGCTATGCCGCAGTCTGGAACTGGTGTTAGTG

TGGAGGCTGTGGATCCCGTTTTCCAGGCTAAAATGTTGGATATGTTAAAA

CAGACTGGAAGGCCTGAAATGGTAGTCGGTTGGTATCACAGCCACCCTGG

CTTTGGCTGCTGGCTTTCTGGCGTTGACATTAATACCCAGCAGAGCTTTG

AAGCCCTTTCGGAAAGAGCAGTAGCAGTAGTAGTGGATCCTATCCAGAGC

GTTAAAGGAAAGGTTGTTATTGATGCTTTCAGACTGATTAATGCTAACAT

GATGGTCTTAGGACACGAACCAAGGCAAACCACTTCAAATCTTGGGCATT

TAAACAAGCCATCTATACAGGCTCTTATTCATGGTCTTAACCGGCATTAC

TACTCAATAACCATTAATTACAGAAAAAATGAACTTGAACAAAGATGCT

GTTGAATTTGCATAAAAAG<u>TCAGGTCTTAAGATGTACGATTATGAAGAAA

AAGAAGAATCAAATTTGGCTGCTACAAAGAGTATGGTTAAGATAGCCGAA

CAGTACTCTAAGAGAATAGAAGAGGAAAAGGAATTAACCGAAGAAGAACT

TAAGACAAGATACGTTGGTAGGCAAGATCCAAAGAAGCACCTTTCCGAAA

CAGCAGATGAGACACTAGAGAACAATATTGTTTCTGTGCTGACGGCGGGT

GTTAATTCAGTGGCAATTAAATAA</u>
Non-underlined sequences are derived from *Xenopus
laevis* cDNA for Rpn11. Underlined sequences are
derived from yeast (*Saccharomyces cerevisiae*)
chromosomal Rpn11.

hRpn11 amino acid sequence demarcated by domain
SEQ ID NO: 3
MDRLLRLGGGMPGLGQGPPTDAPAVDTAEQVYISSLALLKMLKHGRAGVP

MEVMGLMLGEFVDDYTVRVIDVFAMPQSGTGVSVEAVDPVFQAKMLDMLK

QTGRPEMVVGWYHSHPGFGCWLSGVDINTQQSFEALSERAVAVVVDPIQS

VKGKVVIDAFRLINANMMVLGHEPRQTTSNLGHLNKPSIQALIHGLNRHY

YSITINYRKNE<u>LEQKMLLNLHKKSGLKMY</u>*DYEEKEESNLAATKSMVKIAE

QYSKRIEEEKELTEEELKTRYVGRQDPKKHLSETADETLENNIVSVLTAG

VNSVAIK*

Standard font: deubiquitinase catalytic domain.
Underlined: linker domain. Italics: non-human
deubiquitinase proteasome binding domain.

catalytically inactive hRpn11 (AXA) amino acid
sequence
SEQ ID NO: 4
MDRLLRLGGGMPGLGQGPPTDAPAVDTAEQVYISSLALLKMLKHGRAGVP

MEVMGLMLGEFVDDYTVRVIDVFAMPQSGTGVSVEAVDPVFQAKMLDMLK

QTGRPEMVVGWY<u>A</u>S<u>A</u>PGFGCWLSGVDINTQQSFEALSERAVAVVVDPIQS

VKGKVVIDAFRLINANMMVLGHEPRQTTSNLGHLNKPSIQALIHGLNRHY

YSITINYRKNELEQKMLLNLHKKSGLKMYDYEEKEESNLAATKSMVKIAE

QYSKRIEEEKELTEEELKTRYVGRQDPKKHLSETADETLENNIVSVLTAG

VNSVAIK
Underlined: Histidines 113 and 115 are mutated to
alanine in hRpn11 (AXA).

cDNA sequence of catalytically inactive
hRpn11 (AXA)
SEQ ID NO: 5
ATGGACCGACTTTTAAGGCTTGGAGGAGGGATGCCTGGACTTGGCCAGGG

CCCTCCCACTGATGCTCCTGCAGTGGATACTGCCGAACAGGTTTATATCT

CCTCCCTGGCTTTGCTCAAGATGCTAAAACACGGACGAGCTGGTGTCCCA

ATGGAAGTCATGGGACTGATGCTGGGAGAGTTTGTGGATGATTACACAGT

CAGGGTCATTGATGTTTTTGCTATGCCGCAGTCTGGAACTGGTGTTAGTG

TGGAGGCTGTGGATCCCGTTTTCCAGGCTAAAATGTTGGATATGTTAAAA

CAGACTGGAAGGCCTGAAATGGTAGTCGGTTGGTAT<u>GCT</u>AGC<u>GCG</u>CCTGG

CTTTGGCTGCTGGCTTTCTGGCGTTGACATTAATACCCAGCAGAGCTTTG

AAGCCCTTTCGGAAAGAGCAGTAGCAGTAGTAGTGGATCCTATCCAGAGC

GTTAAAGGAAAGGTTGTTATTGATGCTTTCAGACTGATTAATGCTAACAT

GATGGTCTTAGGACACGAACCAAGGCAAACCACTTCAAATCTTGGGCATT

TAAACAAGCCATCTATACAGGCTCTTATTCATGGTCTTAACCGGCATTAC

TACTCAATAACCATTAATTACAGAAAAAATGAACTTGAACAAAGATGCT

GTTGAATTTGCATAAAAAGTCAGGTCTTAAGATGTACGATTATGAAGAAA

AAGAAGAATCAAATTTGGCTGCTACAAAGAGTATGGTTAAGATAGCCGAA

*CAGTACTCTAAGAGAATAGAAGAGGAAAAGGAATTAACCGAAGAAGAACT*

*TAAGACAAGATACGTTGGTAGGCAAGATCCAAAGAAGCACCTTTCCGAAA*

*CAGCAGATGAGACACTAGAGAACAATATTGTTTCTGTGCTGACGGCGGGT*

*GTTAATTCAGTGGCAATTAAATAA*
Sequences in standard font are derived from
*Xenopus laevis* cDNA for Rpn11. Sequences in italics
are derived from yeast (*Saccharomyces cerevisiae*)
chromosomal hRpn11. Underlined: Codons encoding
histidines 113 and 115 are mutated to alanine in
hRpn11 (AXA).

I claim:

1. A nucleic acid encoding a chimeric protein comprising a mammalian deubiquitinase catalytic domain, a linker domain, and a non-human deubiquitinase proteasome binding domain; wherein said chimeric protein is encoded by a nucleic acid sequence having at least 80% identity to SEQ ID NO: 2.

2. The nucleic acid of claim 1, wherein the deubiquitinase is Rpn11.

3. The nucleic acid of claim 1, wherein the linker domain comprises a non-human deubiquitinase linker domain.

4. The nucleic acid of claim 1, wherein the mammalian deubiquitinase catalytic domain is N-terminally fused to the linker domain, and wherein the linker domain is fused adjacent to the C-terminal non-human deubiquitinase proteasome binding domain.

5. The nucleic acid of claim 1, wherein the chimeric protein comprises amino acids 1-215 of SEQ ID NO: 1.

6. The nucleic acid of claim 1, wherein the chimeric protein comprises amino acids 216-232 of SEQ ID NO: 1.

7. The nucleic acid of claim 1, wherein the chimeric protein comprises amino acids 233-306 of SEQ ID NO: 1.

8. A biological cell comprising the nucleic acid sequence of claim 1.

9. The biological cell of claim 8, wherein the biological cell is a yeast cell.

* * * * *

SEQUENCE LISTING

<160> NUMBER OF SEQ ID NOS: 5

<210> SEQ ID NO 1
<211> LENGTH: 307
<212> TYPE: PRT
<213> ORGANISM: Artificial Sequence
<220> FEATURE:
<223> OTHER INFORMATION: Synthetic construct

<400> SEQUENCE: 1

Met Asp Arg Leu Leu Arg Leu Gly Gly Gly Met Pro Gly Leu Gly Gln
1               5                   10                  15

Gly Pro Pro Thr Asp Ala Pro Ala Val Asp Thr Ala Glu Gln Val Tyr
            20                  25                  30

Ile Ser Ser Leu Ala Leu Leu Lys Met Leu Lys His Gly Arg Ala Gly
        35                  40                  45

Val Pro Met Glu Val Met Gly Leu Met Leu Gly Glu Phe Val Asp Asp
    50                  55                  60

Tyr Thr Val Arg Val Ile Asp Val Phe Ala Met Pro Gln Ser Gly Thr
65                  70                  75                  80

Gly Val Ser Val Glu Ala Val Asp Pro Val Phe Gln Ala Lys Met Leu
                85                  90                  95

Asp Met Leu Lys Gln Thr Gly Arg Pro Glu Met Val Val Gly Trp Tyr
            100                 105                 110

His Ser His Pro Gly Phe Gly Cys Trp Leu Ser Gly Val Asp Ile Asn
        115                 120                 125

Thr Gln Gln Ser Phe Glu Ala Leu Ser Glu Arg Ala Val Ala Val Val
    130                 135                 140

Val Asp Pro Ile Gln Ser Val Lys Gly Lys Val Val Ile Asp Ala Phe
145                 150                 155                 160

Arg Leu Ile Asn Ala Asn Met Met Val Leu Gly His Glu Pro Arg Gln
                165                 170                 175

Thr Thr Ser Asn Leu Gly His Leu Asn Lys Pro Ser Ile Gln Ala Leu
            180                 185                 190

Ile His Gly Leu Asn Arg His Tyr Tyr Ser Ile Thr Ile Asn Tyr Arg
        195                 200                 205

Lys Asn Glu Leu Glu Gln Lys Met Leu Leu Asn Leu His Lys Lys Ser
    210                 215                 220

Gly Leu Lys Met Tyr Asp Tyr Glu Glu Lys Glu Ser Asn Leu Ala
225                 230                 235                 240

Ala Thr Lys Ser Met Val Lys Ile Ala Glu Gln Tyr Ser Lys Arg Ile
                245                 250                 255

Glu Glu Glu Lys Glu Leu Thr Glu Glu Leu Lys Thr Arg Tyr Val
            260                 265                 270

Gly Arg Gln Asp Pro Lys Lys His Leu Ser Glu Thr Ala Asp Glu Thr
        275                 280                 285

Leu Glu Asn Asn Ile Val Ser Val Leu Thr Ala Gly Val Asn Ser Val
    290                 295                 300

Ala Ile Lys
305

<210> SEQ ID NO 2
<211> LENGTH: 924
<212> TYPE: DNA
<213> ORGANISM: Artificial Sequence
<220> FEATURE:
<223> OTHER INFORMATION: Synthetic construct

<400> SEQUENCE: 2

```
atggaccgac ttttaaggct tggaggaggg atgcctggac ttggccaggg ccctcccact    60
gatgctcctg cagtggatac tgccgaacag gtttatatct cctccctggc tttgctcaag   120
atgctaaaac acggacgagc tggtgtccca atggaagtca tgggactgat gctgggagag   180
tttgtggatg attacacagt cagggtcatt gatgtttttg ctatgccgca gtctggaact   240
ggtgttagtg tggaggctgt ggatcccgtt ttccaggcta aaatgttgga tatgttaaaa   300
cagactggaa ggcctgaaat ggtagtcggt tggtatcaca gccaccctgg ctttggctgc   360
tggctttctg gcgttgacat taatacccag cagagctttg aagccctttc ggaaagagca   420
gtagcagtag tagtggatcc tatccagagc gttaaggaa aggttgttat tgatgctttc   480
agactgatta atgctaacat gatggtctta ggacacgaac caaggcaaac cacttcaaat   540
cttgggcatt taaacaagcc atctatacag gctcttattc atggtcttaa ccggcattac   600
tactcaataa ccattaatta cagaaaaaat gaacttgaac aaaagatgct gttgaatttg   660
cataaaaagt caggtcttaa gatgtacgat tatgaagaaa agaagaatc aaatttggct   720
gctacaaaga gtatggttaa gatagccgaa cagtactcta agagaataga agaggaaaag   780
gaattaaccg aagaagaact taagacaaga tacgttggta ggcaagatcc aaagaagcac   840
ctttccgaaa cagcagatga gacactagag aacaatattg tttctgtgct gacggcgggt   900
gttaattcag tggcaattaa ataa                                          924
```

<210> SEQ ID NO 3
<211> LENGTH: 307
<212> TYPE: PRT
<213> ORGANISM: Artificial Sequence
<220> FEATURE:
<223> OTHER INFORMATION: Synthetic construct

<400> SEQUENCE: 3

```
Met Asp Arg Leu Leu Arg Leu Gly Gly Gly Met Pro Gly Leu Gly Gln
1               5                   10                  15

Gly Pro Pro Thr Asp Ala Pro Ala Val Asp Thr Ala Glu Gln Val Tyr
            20                  25                  30

Ile Ser Ser Leu Ala Leu Leu Lys Met Leu Lys His Gly Arg Ala Gly
        35                  40                  45

Val Pro Met Glu Val Met Gly Leu Met Leu Gly Glu Phe Val Asp Asp
    50                  55                  60

Tyr Thr Val Arg Val Ile Asp Val Phe Ala Met Pro Gln Ser Gly Thr
65                  70                  75                  80

Gly Val Ser Val Glu Ala Val Asp Pro Val Phe Gln Ala Lys Met Leu
                85                  90                  95

Asp Met Leu Lys Gln Thr Gly Arg Pro Glu Met Val Val Gly Trp Tyr
            100                 105                 110

His Ser His Pro Gly Phe Gly Cys Trp Leu Ser Gly Val Asp Ile Asn
        115                 120                 125

Thr Gln Gln Ser Phe Glu Ala Leu Ser Glu Arg Ala Val Ala Val Val
    130                 135                 140

Val Asp Pro Ile Gln Ser Val Lys Gly Lys Val Val Ile Asp Ala Phe
145                 150                 155                 160

Arg Leu Ile Asn Ala Asn Met Met Val Leu Gly His Glu Pro Arg Gln
                165                 170                 175

Thr Thr Ser Asn Leu Gly His Leu Asn Lys Pro Ser Ile Gln Ala Leu
```

```
                    180                 185                 190
Ile His Gly Leu Asn Arg His Tyr Tyr Ser Ile Thr Ile Asn Tyr Arg
            195                 200                 205

Lys Asn Glu Leu Glu Gln Lys Met Leu Leu Asn Leu His Lys Lys Ser
        210                 215                 220

Gly Leu Lys Met Tyr Asp Tyr Glu Glu Lys Glu Glu Ser Asn Leu Ala
225                 230                 235                 240

Ala Thr Lys Ser Met Val Lys Ile Ala Glu Gln Tyr Ser Lys Arg Ile
            245                 250                 255

Glu Glu Glu Lys Glu Leu Thr Glu Glu Glu Leu Lys Thr Arg Tyr Val
        260                 265                 270

Gly Arg Gln Asp Pro Lys Lys His Leu Ser Glu Thr Ala Asp Glu Thr
            275                 280                 285

Leu Glu Asn Asn Ile Val Ser Val Leu Thr Ala Gly Val Asn Ser Val
        290                 295                 300

Ala Ile Lys
305

<210> SEQ ID NO 4
<211> LENGTH: 307
<212> TYPE: PRT
<213> ORGANISM: Artificial Sequence
<220> FEATURE:
<223> OTHER INFORMATION: Synthetic construct

<400> SEQUENCE: 4

Met Asp Arg Leu Leu Arg Leu Gly Gly Gly Met Pro Gly Leu Gly Gln
1               5                   10                  15

Gly Pro Pro Thr Asp Ala Pro Ala Val Asp Thr Ala Glu Gln Val Tyr
            20                  25                  30

Ile Ser Ser Leu Ala Leu Leu Lys Met Leu Lys His Gly Arg Ala Gly
        35                  40                  45

Val Pro Met Glu Val Met Gly Leu Met Leu Gly Glu Phe Val Asp Asp
    50                  55                  60

Tyr Thr Val Arg Val Ile Asp Val Phe Ala Met Pro Gln Ser Gly Thr
65                  70                  75                  80

Gly Val Ser Val Glu Ala Val Asp Pro Val Phe Gln Ala Lys Met Leu
                85                  90                  95

Asp Met Leu Lys Gln Thr Gly Arg Pro Glu Met Val Val Gly Trp Tyr
            100                 105                 110

Ala Ser Ala Pro Gly Phe Gly Cys Trp Leu Ser Gly Val Asp Ile Asn
        115                 120                 125

Thr Gln Gln Ser Phe Glu Ala Leu Ser Glu Arg Ala Val Ala Val Val
    130                 135                 140

Val Asp Pro Ile Gln Ser Val Lys Gly Lys Val Val Ile Asp Ala Phe
145                 150                 155                 160

Arg Leu Ile Asn Ala Asn Met Met Val Leu Gly His Glu Pro Arg Gln
                165                 170                 175

Thr Thr Ser Asn Leu Gly His Leu Asn Lys Pro Ser Ile Gln Ala Leu
            180                 185                 190

Ile His Gly Leu Asn Arg His Tyr Tyr Ser Ile Thr Ile Asn Tyr Arg
        195                 200                 205

Lys Asn Glu Leu Glu Gln Lys Met Leu Leu Asn Leu His Lys Lys Ser
    210                 215                 220

Gly Leu Lys Met Tyr Asp Tyr Glu Glu Lys Glu Glu Ser Asn Leu Ala
```

-continued

```
                    225                 230                 235                 240
Ala Thr Lys Ser Met Val Lys Ile Ala Glu Gln Tyr Ser Lys Arg Ile
                245                 250                 255
Glu Glu Glu Lys Glu Leu Thr Glu Glu Leu Lys Thr Arg Tyr Val
            260                 265                 270
Gly Arg Gln Asp Pro Lys Lys His Leu Ser Glu Thr Ala Asp Glu Thr
            275                 280                 285
Leu Glu Asn Asn Ile Val Ser Val Leu Thr Ala Gly Val Asn Ser Val
            290                 295                 300
Ala Ile Lys
305

<210> SEQ ID NO 5
<211> LENGTH: 924
<212> TYPE: DNA
<213> ORGANISM: Artificial Sequence
<220> FEATURE:
<223> OTHER INFORMATION: Synthetic construct

<400> SEQUENCE: 5
atggaccgac ttttaaggct tggaggaggg atgcctggac ttggccaggg ccctcccact      60
gatgctcctg cagtggatac tgccgaacag gtttatatct cctccctggc tttgctcaag     120
atgctaaaac acggacgagc tggtgtccca atggaagtca tgggactgat gctgggagag     180
tttgtggatg attacacagt cagggtcatt gatgttttg ctatgccgca gtctggaact      240
ggtgttagtg tggaggctgt ggatcccgtt ttccaggcta aatgttgga tatgttaaaa      300 cagactggaa ggcctgaaat ggtagtcggt tggtatgcta gcgcgcctgg ctttggctgc     360
tggctttctg gcgttgacat taatacccag cagagctttg aagccctttc ggaaagagca     420
gtagcagtag tagtggatcc tatccagagc gttaaggaa aggttgttat tgatgctttc      480
agactgatta atgctaacat gatggtctta ggacacgaac caaggcaaac cacttcaaat     540
cttgggcatt taaacaagcc atctatacag gctcttattc atggtcttaa ccggcattac     600
tactcaataa ccattaatta cagaaaaaat gaacttgaac aaaagatgct gttgaatttg     660
cataaaaagt caggtcttaa gatgtacgat tatgaagaaa agaagaatc aaatttggct      720 gctacaaaga gtatggttaa gatagccgaa cagtactcta agagaataga agaggaaaag     780
gaattaaccg aagaagaact taagacaaga tacgttggta ggcaagatcc aaagaagcac     840
ctttccgaaa cagcagatga gacactagag aacaatattg tttctgtgct gacggcgggt     900
gttaattcag tggcaattaa ataa                                            924
```